United States Patent [19]

Iwata et al.

[11] Patent Number: 5,180,670
[45] Date of Patent: Jan. 19, 1993

[54] METHOD FOR PURIFICATION OF MITOMYCIN C

[75] Inventors: Satoshi Iwata; Michio Shiomi, both of Hofu, Japan

[73] Assignee: Kyowa Hakko Kogyo, Ltd., Tokyo, Japan

[21] Appl. No.: 629,453

[22] Filed: Dec. 18, 1990

[51] Int. Cl.$^5$ .................. C12P 17/18; A01N 43/38; C07D 487/00

[52] U.S. Cl. .................. 435/119; 548/422; 514/410

[58] Field of Search .............. 210/692; 435/121, 119; 514/410; 548/422

[56] References Cited

U.S. PATENT DOCUMENTS 3,660,578  5/1972  Hata et al. .................. 424/274

FOREIGN PATENT DOCUMENTS 61-9094  6/1961  Japan .

OTHER PUBLICATIONS

Water's Chromatography and Supplies Catalog, pp. 4 and 24.
Merck Index, Ref. 6079.

Primary Examiner—Douglas W. Robinson
Assistant Examiner—Sandra Saucier
Attorney, Agent, or Firm—Antonelli, Terry, Stout & Kraus

[57] ABSTRACT

A method for purification of mitomycin C comprises;
a. a step of treating the culture of a mitomycin C-producing microorganism with reverse phase adsorption resin to adsorb mitomycin C onto the resin;
b. a step of eluting mitomycin C with ethyl acetate out of the resin;
c. a step of adding phosphate buffer to the eluate and then evaporating ethyl acetate;
d. a step of passing, under pressure, the residue remaining after the evaporation through a column packed with a reverse phase adsorbent having a small particle diameter to adsorb mitomycin C onto the resin;
e. a step of eluting mitomycin C with aqueous methanol out of the resin under pressure;
f. a step of treating the eluate with a reverse phase adsorption resin to adsorb mitomycin C onto the resin;
g. a step of eluting mitomycin C with methanol out of the resin; and,
h. a step of concentrating the methanol eluate to crystallize mitomycin C.

By this method, mitomycin C can be efficiently purified in an industrial scale.

7 Claims, No Drawings

METHOD FOR PURIFICATION OF MITOMYCIN C

BACKGROUND OF THE INVENTION

The present invention relates to a method for purification of mitomycin C from the culture of a mitomycin C-producing microorganism.

Mitomycin C is an anti-tumor antibiotic obtained by culturing a microorganism belonging to the species *Streptomyces caespitosus* and has been clinically applied for many years.

For purification of mitomycin C from the culture obtained by culturing the microorganism described above, there are known the activated carbon adsorption method which comprises adding an activated carbon to the culture filtrate obtained by removing cells to adsorb mitomycin C thereon and eluting mitomycin C with an organic solvent; or a purification method which comprises extracting mitomycin C contained in the culture filtrate with an organic solvent, and subjecting the resulting concentrate of mitomycin C to alumina chromatography or counter current distribution (Method A: Japanese Published Unexamined Patent Application No. 17897/60, U.S. Pat. No. 3,660,578).

As an improvement of the above method, there has been known a method which comprises adsorbing the culture filtrate onto a reverse phase adsorption resin; eluting mitomycin C with a solvent such as acetone, methanol, ethanol, etc.; concentrating the eluate to remove the solvent; saturating the concentrate with sodium chloride to dissolve the saturated concentrate in chloroform; applying the chloroform extract to alumina column chromatography; eluting the adsorption zone of mitomycin C with methanol; and concentrating the eluate; adding ether, petroleum ether, benzine or ligroin to the concentrate to obtain crystals of mitomycin C (Method B: Japanese Published Examined Patent Application No. 9094/61).

Method A described above encounters such problems that operations such as the elution after adsorption onto activated carbon, the extraction with an organic solvent, etc. are inefficient and thus a recovery yield of mitomycin C is low, etc.

Also in Method B, for example, Duolite S-30 (Duolite Co., Ltd.) which is specifically shown as the reverse phase adsorption resin has a poor adsorbability of mitomycin C so that large quantities of the resin and solvent should be used. Upon the extraction with chloroform, extraction efficiency is low so that a large quantity of chloroform is used and the extraction operation is repeated. Furthermore, the steps of eluting mitomycin C and isolating mitomycin C from the alumina adsorption zone subsequent to chromatography involve complicated operations and are also undesired in view of working environments. In addition, the purity of the resulting eluate is not so high. The crystals obtained from the eluate are not satisfactory in purity, unless they are recrystallized. Moreover, a time period required for the overall steps of purification is prolonged. Thus, the prior art methods encounter various problems.

Therefore, an improve method is always in demand for purification of mitomycin C in an industrial scale, in view of operability, productivity, etc.

SUMMARY OF THE INVENTION

According to the present invention, an advantageous method for purification of mitomycin C in an industrial scale is provided. That is, the present invention relates to a method for purification of mitomycin C which comprises:

a. a step of treating the culture of a mitomycin C-producing microorganism with reverse phase adsorption resin to adsorb mitomycin C onto the resin;

b. a step of eluting mitomycin C with ethyl acetate out of the resin;

c. a step of adding phosphate buffer to the eluate and then evaporating ethyl acetate;

d. a step of passing, under pressure, the residue remaining after the evaporation through a column packed with a reverse phase adsorbent having a small particle diameter to adsorb mitomycin C onto the resin;

e. a step of eluting mitomycin C with aqueous methanol out of the resin under pressure;

f. a step of treating the eluate with a reverse phase adsorption resin to adsorb mitomycin C onto the resin;

g. a step of eluting mitomycin C with methanol out of the resin; and, h. a step of concentrating the methanol eluate to crystallize mitomycin C.

DETAILED DESCRIPTION OF THE INVENTION

Hereafter the method for purification of mitomycin C according to the present invention is described in detail.

a) The culture filtrate obtained by separating cells from the culture obtained by known methods (for example, Japanese Published Examined Patent Application No. 17897/60) is cooled. After its pH is adjusted to 6.8 to 7.0 with phosphoric acid, the culture filtrate is passed through the reverse phase adsorption resin.

Herein, polystyrene divinylbenzene type resin is preferably used as the reverse phase adsorption resin, in place of Doulite S-30, a phenolic resin which has been used so far. A specific example of the resin is DIAION SP-207 (Product of Mitsubishi Kasei Corporation). An amount of the resin used is in a range of 300 to 500 ml, generally 400 ml, in the case of DIAION SP-207, per 1 g of mitomycin C; whereas Duolite S-30 requires 3 liters.

b) Then, the resin onto which mitomycin C has been adsorbed is washed followed by elution with ethyl acetate. An amount of ethyl acetate used for the elution is generally 1.5 to 2 liters per 1 liter of the resin.

By using DIAION SP-207 as the adsorbing resin in place of Duolite S-30, adsorbability of mitomycin C onto the resin is improved and an amount of the elution solvent used is greatly reduced.

c) Next, 1- to 2-fold amount of phosphate buffer (0.01 mol/l of sodium phosphate) having pH of 6.5 to 8.0 is added to the resulting ethyl acetate eluate. Ethyl acetate is evaporated under reduced pressure to give phosphate buffer containing mitomycin C. In this treatment procedure, a large quantity of the organic solvent is not required and the operation is simple, as compared to the conventional extraction with chloroform. Further by using such buffer, possible decomposition of mitomycin C during the concentration can also be prevented.

d) and e) The thus prepared phosphate buffer containing mitomycin C is passed through a column packed with the reverse phase adsorbent having a small particle diameter. After washing with water, the adsorbed mitomycin C is eluted with aqueous methanol. In order to separate mitomycin C from larger amounts of a sample in a high yield with good separation in a short period of time, it is generally advantageous to conduct there operations under pressure (so-called high performance liquid chromatography; hereafter referred to as HPLC method).

As the reverse phase adsorbent suited for treating a large quantity of samples in an industrial scale in the HPLC method, for example, octadecylated silica gel is used. Specific examples of the silica gel include ODS-AQ60, ODSA-AQ120 (a product of Yamamura Chemical) and the like.

The packing agent (adsorbent) has a particle diameter of 10 to 200 $\mu$, preferably about 50 $\mu$, from viewpoints of the amount of a sample treated, separation property, etc. The adsorbent is used generally in an amount of 200 to 300 ml per 1 g of mitomycin C. The pressure upon adsorption and elution of mitomycin C is 10 to 50 $kg/cm^2$. The concentration of aqueous methanol used for elution is preferably 20 to 40%. A flow rate upon elution is SV 1 to 5.

The HPLC method is superior to conventional alumina column chromatography in degree of purification, operability, working environment, etc.

f) Next, in order to concentrate mitomycin C diluted by separation on chromatography, the concentration of methanol in the aqueous methanol solution containing the elution fraction of mitomycin C is adjusted to 10% or less, which is again passed through a small quantity of reverse phase adsorption resin. As the adsorption resin, polystyrene divinylbenzene type resin is preferred, as described above and, for example, DIAION SP-207 is used. An amount of the resin used is 80 to 100 ml per 1 g of mitomycin C.

g) The elution is made with methanol. In general, 2 to 3 liters of methanol is used per 1 liter of the resin.

h) The methanol eluted solution containing the fraction of mitomycin C is concentrated to about 200 to 250 g/l under reduced pressure. By allowing the concentrate to stand at 5 to 10° C. for 5 to 10 hours, mitomycin C is crystallized. The crystals are taken by filtration and dried to give mitomycin C having a high purity.

In the prior art, the crystals were further recrystallized following the chromatographic treatment to obtain the product of high purity. In the present crystallization method, mitomycin C of high purity comparable to the prior art product can be obtained without recrystallization.

The method for purification of mitomycin C according to the present invention is also characterized by improved yield of purification, shortened time for the operation, etc., in addition to the characteristic feature described above.

The embodiments of the present invention are explained by referring to the following example and reference example.

In the example and reference example, the purity of mitomycin C was analyzed by HPLC under the conditions described below.
Column: YMC AM-312 ODS, 6$\phi$ × 150 mmL
Eluent: 20% methanol: 80% 0.01M ammonium acetate, pH 6.5
Elution speed: 1 ml/min
Temperature: 35° C.
Detection: UV (254 nm)

EXAMPLE

To 4500 liters of the culture containing 500 g of mitomycin C was added 300 kg of Radiolite #500 (Showa Chemical Industry) as a filter aid. The mixture was filtered through a filter press. After phosphoric acid was added to 5000 liters of the resulting filtrate to adjust pH to 7, the mixture was passed through a column packed with 200 liters of DIAION SP-207 at a flow rate of 1000 liters/hr. After washing the column with water, 400 liters of ethyl acetate flowed at a flow rate of 200 liters/hr to give 400 liters of the eluate. The eluate contained 436 g of mitomycin C. After 400 liters of phosphate buffer of pH 7.5 was added to the eluate, the mixture was concentrated under reduced pressure to evaporate ethyl acetate. Under pressure of 20 $kg/cm^2$, 300 liters of the thus obtained aqueous solution was passed through an industrial HPLC column packed with 80 liters of ODS-A120-S50 at a flow rate of 200 liters/hr. After washing with 80 liters of 10% methanol aqueous solution, elution was performed with 600 liters of 30% methanol aqueous solution at a flow rate of SV 3. To 80 liters of the fraction containing 406 g of mitomycin C was added 160 liters of water. The mixture was passed through a column packed with 30 liters of DIAION SP-207 at a flow rate of 150 liters/hr. After water in the resin flowed out, elution was made with methanol to give 60 liters of the methanol solution containing 380 g (purity of 97.6%) of mitomycin C. The solution was concentrated to 1.9 liters under reduced pressure followed by ripening at 5° C. for 10 hours. The resulting crystals were taken by filtration and dried in vacuum to give 350 g (purity of 99.7%) of mitomycin C.

REFERENCE EXAMPLE

Phosphoric acid was added to 5000 liters of the culture obtained in a manner similar to Example thereby to adjust pH to 7, and the mixture was passed through a column packed with 1500 liters of Duolite S-30 at a flow rate of 2000 liters/hr. After washing the column with water, acetone was passed through at a flow rate of 2000 liters/hr to give 2000 liters of the eluate. The eluate contained 434 g of mitomycin C. After 500 liters of water was added, the mixture was concentrated under reduced pressure to evaporate acetone. Thus, 300 liters of the aqueous solution was obtained. 35 kg of sodium chloride was dissolved in the aqueous solution. Then 300 liters of chloroform was added to the solution followed by stirring. After the chloroform layer was separated, chloroform was again added to the aqueous layer. After stirring, the chloroform layer was separated. This procedure was repeated 5 times to give 1500 liters of the chloroform extract. Then content of mitomycin C was 415 g. After the extract was divided into ten 150 liter-portions, the portion was passed through each of 10 columns packed with 3 liters of alumina which has been previously dried at 120° C. for 20 hours for its activation. Then, 4 liters of chloroform containing 3% methanol was passed through each column. After the solvent was withdrawn, the alumina layer was removed from the column and the adsorption zones of mitomycin C from the 10 columns were cut out. By stirring in 50 liters of methanol for 30 minutes and filtering, the filtrate containing 336 g (purity of 80.4%) of mitomycin C was obtained. The filtrate was concentrated to 1.7 liters under reduced pressure followed by ripening at 5° C. for 10 hours. The resulting crystals were taken by filtration and dried in vacuum to give 296 g (purity of 97.4%) of mitomycin C.

The crystals were dissolved in 90 liters of methanol and the solution was concentrated to 1.5 liters under reduced pressure followed by ripening at 5° C. for 10 hours. The recrystallized crystals were taken by filtration and dried in vacuum to give 272 g (purity of 99.7%) of mitomycin C.

According to the present invention, the method for efficient purification of mitomycin C in an industrial scale is provided.

While the invention has been described in detail and with reference to specific embodiments thereof, it is apparent to one skilled in the art that various changes and modifications can be made therein without departing from the spirit and the scope of the present invention.

What is claimed is:

1. A method for purification of mitomycin C which comprises the steps of:
   a. treating the culture of a mitomycin C-producing microorganism with polystyrene divinylbenzene type resin to adsorb mitomycin C onto said resin;
   b. eluting mitomycin C with ethyl acetate out of said resin;
   c. adding phosphate buffer to said eluate and then evaporating ethyl acetate;
   d. passing, under pressure, the residual remaining after the evaporation through a column packed with a reverse phase adsorbent having a small particle diameter to adsorb mitomycin C onto said adsorbent;
   e. eluting mitomycin C with aqueous methanol out of said adsorbent under pressure;
   f. treating said eluate with polystyrene divinylbenzene type resin to adsorb mitomycin C onto said resin;
   g. eluting mitomycin C with methanol out of said resin; and
   h. concentrating the methanol eluate to crystallize mitomycin C.

2. The method according to claim 1, wherein said polystyrene divinylbenzene type resin used in steps a. and f. is DIAION ® SP-207.

3. The method according to claim 1, step c., wherein the pH of said phosphate buffer is 6.5 to 8.0.

4. The method according to claim 1, step d., wherein said reverse phase adsorbent having a small particle diameter used as a packing agent for the column treated under pressure is octadecylated silica gel.

5. The method according to claim 4, wherein said octadecylated silica gel has a particle diameter of 10 to 200 $\mu$.

6. The method according to claim 1, steps d. and e., wherein said pressure upon passage of phosphate buffer containing mitomycin C and upon elution with aqueous methanol is 10 to 50 kg/cm$^2$.

7. The method according to claim 1, step e., wherein the concentration of aqueous methanol for the elution is 20 to 40%.

* * * * *